US008404473B2

(12) United States Patent
Kilian et al.

(10) Patent No.: US 8,404,473 B2
(45) Date of Patent: Mar. 26, 2013

(54) CYANOBACTERIAL ISOLATES HAVING AUTO-FLOCCULATION AND SETTLING PROPERTIES

(75) Inventors: Oliver Kilian, Alameda, CA (US); Bertrand Vick, Emeryville, CA (US)

(73) Assignee: Aurora Algae, Inc., Hayward, CA (US)

( * ) Notice: Subject to any disclaimer, the term of this patent is extended or adjusted under 35 U.S.C. 154(b) by 460 days.

(21) Appl. No.: 12/495,581

(22) Filed: Jun. 30, 2009

(65) Prior Publication Data
US 2010/0330643 A1   Dec. 30, 2010

(51) Int. Cl.
C12N 1/00 (2006.01)
C12N 1/12 (2006.01)
C12P 7/00 (2006.01)
C07H 21/02 (2006.01)

(52) U.S. Cl. .................. 435/243; 435/257.1; 435/132; 536/23.1

(58) Field of Classification Search .................. None
See application file for complete search history.

(56) References Cited

U.S. PATENT DOCUMENTS

| | | |
|---|---|---|
| 1,926,780 A | 9/1933 | Lippincott |
| 3,468,057 A | 9/1969 | Buisson |
| 4,003,337 A | 1/1977 | Moore |
| 4,267,038 A | 5/1981 | Thompson |
| 4,365,938 A | 12/1982 | Warinner |
| 4,535,060 A | 8/1985 | Comai |
| 4,658,757 A | 4/1987 | Cook |
| 5,478,208 A | 12/1995 | Kasai |
| 5,527,456 A | 6/1996 | Jensen |
| 5,661,017 A | 8/1997 | Dunahay et al. |
| 5,668,298 A | 9/1997 | Waldron et al. |
| 6,117,313 A | 9/2000 | Goldman |
| 6,143,562 A | 11/2000 | Trulson et al. |
| 6,372,460 B1 | 4/2002 | Gladue et al. |
| 6,736,572 B2 | 5/2004 | Geraghty |
| 7,381,326 B2 | 6/2008 | Haddas |
| 2005/0170479 A1 | 8/2005 | Weaver et al. |
| 2006/0045750 A1 | 3/2006 | Stiles |
| 2006/0101535 A1 | 5/2006 | Forster et al. |
| 2006/0122410 A1 | 6/2006 | Fichtali et al. |
| 2008/0194029 A1 | 8/2008 | Hegemann et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2010/0068772 A1 | 3/2010 | Downey |
| 2010/0210003 A1 | 8/2010 | King |
| 2010/0210832 A1 | 8/2010 | Kilian et al. |

OTHER PUBLICATIONS

Santin-Montanaya, I. Optimal growth of *Dunaliella primolecta* in axenic conditions to assay herbicides, Chemosphere, 66, Elsevier 2006, pp. 1315-1322.
Felix, R. Use of the cell wall-less alga *Dunaliella bioculata* in herbicide screening tests, Annals of Applied Biology, 113, 1988, pp. 55-60.
Janssen, M. Photosynthetic efficiency of *Dunaliella tertiolecta* under short light/dark cycles, Enzyme and Microbial Technology, 29, 2001, pp. 298-305.
Saenz, M.E. Effects of Technical Grade and a Commercial Formulation of Glyphosate on Algal Population Growth, Bulletin of Environmental Contamination Toxicology, 1997, pp. 638-644.
Prein et al., "A Novel Strategy for Constructing N-terminal Chromosomal Fusions to Green Fluorescent Protein in the Yeast *Saccharomyces cerevisiae*," FEBS Letters 485 (2000) 29-34.
Wendland et al., "PCR-Based Methods Facilitate Targeted Gene Manipulations and Cloning Procedures," Curr. Gen. (2003) 44: 115-123.
Kindle, et al., "Stable Nuclear Transformation of Chlamydomonas Using the Chlamydonnonas Gene for Nitrate Reductase," The Journal of Cell Biology 109(6, part 1): 2589-2601, 1989.
Endo et al., "Inactivation of Blasticidin S by *Bacillus cereus* II. Isolation and Characterization of a Plasmid, pBSR 8, From *Bacillus cereus*," The Journal of Antibiotics 41(2): 271-273 (1988).
Schiedlmeier et al., "Nuclearn Transformation of Volvox Carteri," Proceedings of the National Academy of Sciences USA 91(11): 5080-5084 (May 1994).
Hallmann et al., "Genetic Engineering of the Multicellular Green Alga Volvox: A Modified and Multiplied Bacterial Antibiotic Resistance Gene as a Dominant Selectable Marker," The Plant Journal 17(1): 99-109 (Jan. 1999).
Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.
Chen et al. Conditional Production of a Functional Fish Growth Hormonal in the Transgenic Line of *Nannochloropsis oculata (Eustigmatophyceae)*. J. Phycol. Jun. 2008 vol. 44 No. 3 pp. 768-776. Especially abstract.
Nelson et al. Targeted Disruption of the NIT8 Gene in *Chlamydomonas reinhardtii*. Mol. Cell Bio. Oct. 1995, vol. 15, No. 10, pp. 5762-5769. Especially abstract and p. 5763 left col. para 2.
Grima et al. "Recovery of Microalgal Biomass in Metabolites: Process Options and Economics "Biotechnology Advances 20 (2003) 491-515.
Knuckey et al. "Production of Microalgal Concentrates by Flocculation and their Assessment as Aquaculture Feeds, " Aquaculturel Engineering 35 (2006) 300-313.

*Primary Examiner* — Yong Pak
(74) *Attorney, Agent, or Firm* — Carr & Ferrell LLP

(57) ABSTRACT

Provided herein are exemplary methods for production of biomass with a cyanobacterial isolate having auto-flocculation properties. One exemplary method includes isolating a cyanobacterial strain having a 16S ribosomal RNA sequence corresponding to SEQ. ID. NO. 1 herein, inoculating an algae cultivation system with the cyanobacterial strain, growing the cyanobacterial strain, and harvesting the biomass produced by the cyanobacterial strain. According to a further method, the harvesting of the biomass comprises ceasing agitation of the algae cultivation system, and pooling a slurry of the biomass produced by the cyanobacterial strain. In a further method, the harvesting of the biomass may comprise ceasing agitation within the algae cultivation system and/or allowing the biomass produced by the cyanobacterial strain to settle to near or at a bottom of the algae cultivation system. Also provided herein are exemplary cyanobacterial strains having flocculation properties for production of a biomass.

4 Claims, 3 Drawing Sheets

```
TGCTACCATGCAGTCGAACGGGCTCTTCGGAGCTAGTGGCG
GACGGGTGAGGAACGCGTGAGAACCTGCCTCAAG
GTCGGGGACAACAGTTGGAAACGACTGCTAATACCGGATG
AGCCGAATAGGTAAAAGATTTATCGCCTAGAGAGGGCTC
GCGTCTGATTAGCTAGATGGTGAGGTAAAGGCTTACCATG
GCGACGATCAGTAGCTGGTCTGAGAGGATGAGCAGCCACA
CTGGGACTGAGACACGGCCCAGACTCCTACGGGAGGCAGC
AGTGGGGAATTTTCCGCAATGGGCGAAAGCCTGACGGAGC
AATACCGCGTGAGGGAGGAAGGCTCTTGGGTTGTAAACCT
CAAAACTTAGGGAAGAAAAAAATGACGGTACCTAATGTAA
GCATCGGCTAACTCCGTGCCAGCAGCCGCGGTAATACGGA
GGATGCAAGCGTTATCCGGAATCATTGGGCGTAAAGAGTC
CGTAGGTGGCACTTCAAGTCTGCTTTCAAAGACCGAAGCTC
AACTTCGGAAAGGGAGTGGAAACTGAAGAGCTAGAGTAT
AGTAGGGGTAGAGGGAATTCCTAGTGTAGCGGTGAAATGC
GTAGAGATTAGGAAGAACACCAGTGGCGAAGGCGCTCTAC
TGGGCATATACTGACACTGAGGGACGAAAGCTAGGGGAGC
GAAAGGGATTAGATACCCTGTAGTCCTAGCGGTAAACGA
TGGATACTAGGCGTAGTGCTGTTAGAAGGACTGTGCCGAA
GCTAACGCGTTAAGTATCCCGCCTGGGGAGTACGCACGCA
AGTGTGAAACTCAAAGGAATTGACGGGGACCCGCACAAGC
GGTGGAGTATGTGGTTTAATTCGATGCAACGCGAAGAACC
TTACCAAGGCTTGACATCCTGCGAATCTTAATGAAAGTTTG
AGAGTGCCTAAGGAACGCAAAGACAGGTGGTGCATGGCT
GTCNTCANCTCGTGTCGTGANATGTTGGGTTAAGTCCCGCA
NCGAGCGCANCCCTCGTCNTTATTGCCAGCATNANTTGG
GGACTCTAGGGAAACCCCGGGAAAACTCNGAAGAAGGGG
GGATGACNTCAGTCACNTGCCCNTACTNTTGGGCTACCCCC
TTACTAAATGTTGG
```

FIG. 2

SEQUENCE LISTING

<160> NUMBER OF SEQ ID NOS: 1

<210> SEQ ID NO 1
<211> LENGTH: 1129
<212> TYPE: DNA
<213> ORGANISM: Cyanobacteria
<220> FEATURE:
<221> NAME/KEY: misc_feature

```
<222> LOCATION: (959)..(959)
<223> OTHER INFORMATION: n is a, c, g, t or u
<220> FEATURE:
<221> NAME/KEY: misc_feature
<222> LOCATION: (963)..(963)
<223> OTHER INFORMATION: n is a, c, g, t or u
<220> FEATURE:
<221> NAME/KEY: misc_feature
<222> LOCATION: (976)..(976)
<223> OTHER INFORMATION: n is a, c, g, t or u
<220> FEATURE:
<221> NAME/KEY: misc_feature
<222> LOCATION: (997)..(997)
<223> OTHER INFORMATION: n is a, c, g, t or u
<220> FEATURE:
<221> NAME/KEY: misc_feature
<222> LOCATION: (1006)..(1006)
<223> OTHER INFORMATION: n is a, c, g, t or u
<220> FEATURE:
<221> NAME/KEY: misc_feature
<222> LOCATION: (1015)..(1015)
<223> OTHER INFORMATION: n is a, c, g, t or u
<220> FEATURE:
<221> NAME/KEY: misc_feature
<222> LOCATION: (1029)..(1029)
<223> OTHER INFORMATION: n is a, c, g, t or u
<220> FEATURE:
<221> NAME/KEY: misc_feature
<222> LOCATION: (1031)..(1031)
<223> OTHER INFORMATION: n is a, c, g, t or u
<220> FEATURE:
<221> NAME/KEY: misc_feature
<222> LOCATION: (1064)..(1064)
<223> OTHER INFORMATION: n is a, c, g, t or u
<220> FEATURE:
<221> NAME/KEY: misc_feature
<222> LOCATION: (1082)..(1082)
<223> OTHER INFORMATION: n is a, c, g, t or u
<220> FEATURE:
<221> NAME/KEY: misc_feature
<222> LOCATION: (1091)..(1091)
<223> OTHER INFORMATION: n is a, c, g, t or u
<220> FEATURE:
<221> NAME/KEY: misc_feature
<222> LOCATION: (1097)..(1097)
<223> OTHER INFORMATION: n is a, c, g, t or u
<220> FEATURE:
<221> NAME/KEY: misc_feature
<222> LOCATION: (1102)..(1102)
<223> OTHER INFORMATION: n is a, c, g, t or u

<400> SEQUENCE: 1
tgctaccatg cagtcgaacg ggctcttcgg agctagtggc ggacgggtga ggaacgcgtg      60
agaacctgcc tcaaggtcgg ggacaacagt tggaaacgac tgctaatacc ggatgagccg     120
aataggtaaa agatttatcg cctagagagg ggctcgcgtc tgattagcta gatggtgagg     180
taaaggctta ccatggcgac gatcagtagc tggtctgaga ggatgagcag ccacactggg     240
actgagacac ggcccagact cctacgggag gcagcagtgg ggaattttcc gcaatgggcg     300
aaagcctgac ggagcaatac cgcgtgaggg aggaaggctc ttgggttgta aacctcaaaa     360
cttagggaag aaaaaaatga cggtacctaa tgtaagcatc ggctaactcc gtgccagcag     420
ccgcggtaat acggaggatg caagcgttat ccggaatcat tgggcgtaaa gagtccgtag     480
gtggcacttc aagtctgctt tcaaagaccg aagctcaact tcggaagggg agtggaaact     540
gaagagctag agtatagtag gggtagaggg aattcctagt gtagcggtga aatgcgtaga     600
gattaggaag aacaccagtg gcgaaggcgc tctactgggc atatactgac actgagggac     660
gaaagctagg ggagcgaaag ggattagata cccctgtagt cctagcggta acgatggat     720 actaggcgta gtgctgttag aaggactgtg ccgaagctaa cgcgttaagt atcccgcctg     780
gggagtacgc acgcaagtgt gaaactcaaa ggaattgacg ggacccgca caagcggtgg     840
```

-continued

```
agtatgtggt ttaattcgat gcaacgcgaa gaaccttacc aaggcttgac atcctgcgaa    900
tcttaatgaa agtttgagag tgcctaagga acgcaaagac aggtggtgca tggctgtcnt    960
canctcgtgt cgtganatgt tgggttaagt cccgcancga gcgcanccct cgtcnttatt    1020
gccagcatna nttggggact ctagggaaac cccgggaaaa ctcngaagaa ggggggatga    1080
cntcagtcac ntgcccntac tnttgggcta ccccttact aaatgttgg                 1129
```

CYANOBACTERIAL ISOLATES HAVING AUTO-FLOCCULATION AND SETTLING PROPERTIES

REFERENCE TO SEQUENCE LISTINGS

The present application is filed with sequence listing(s) attached hereto and incorporated by reference.

BACKGROUND OF THE INVENTION

1. Field of the Invention

This invention relates to algae cultivation systems, and more specifically to cyanobacterial isolates having auto-flocculation and settling properties.

2. Description of Related Art

The large-scale cultivation of organisms in open ponds presents some formidable challenges including the harvesting of biomass grown in the ponds. For photosynthetic micro-organisms, the ratio of biomass-to-liquid media produced may be very low, sometimes on a scale of only a few milligrams of biomass per liter. Accordingly, the costs associated with separating the biomass from the liquid media may be prohibitively expensive. Consequently, there is a need for algae biomass production with cyanobacterial isolates having auto-flocculation and settling properties.

SUMMARY OF THE INVENTION

Provided herein are exemplary methods for production of biomass with a cyanobacterial isolate having auto-flocculation properties. One exemplary method includes isolating a cyanobacterial strain having a 16S ribosomal RNA sequence corresponding to SEQ. ID. NO. 1 herein, inoculating an algae cultivation system with the cyanobacterial strain, growing the cyanobacterial strain, and harvesting the biomass produced by the cyanobacterial strain. According to a further method, the harvesting of the biomass comprises ceasing agitation of the algae cultivation system, and pooling a slurry of the biomass produced by the cyanobacterial strain. Additionally, the algae cultivation system may include an aqueous environment, wherein the aqueous environment includes seawater and/or freshwater. Further, the aqueous environment may be in a photobioreactor, a pond, or a vessel. In a further method, the harvesting of the biomass may comprise ceasing agitation within the algae cultivation system and/or allowing the biomass produced by the cyanobacterial strain to settle to near or at a bottom of the algae cultivation system.

Also provided herein are exemplary cyanobacterial strains having flocculation properties for production of a biomass. According to one exemplary embodiment, a cyanobacterial strain comprises a 16S ribosomal RNA sequence corresponding to SEQ. ID. NO. 1. In another embodiment, the 16S ribosomal RNA sequence is at least ninety-nine percent (99%) similar to the 16S ribosomal RNA sequence shown in SEQ. ID. NO. 1. Additionally, the various cyanobacterial strains may be grown in an algae cultivation system. The biomass produced by the various exemplary strains may be harvested by ceasing agitation of the algae cultivation system. Additionally, the biomass produced by the strain may be harvested by the biomass settling to at or near the bottom of the algae cultivation system.

BRIEF DESCRIPTION OF THE DRAWINGS

FIG. 2 shows an exemplary 16S ribosomal RNA gene sequence (SEQ. ID. NO. 1) for an exemplary cyanobacterial isolate.

DETAILED DESCRIPTION OF THE INVENTION

*Spirulina* (a cyanobacterium) and *Dunaliella salina* (a microalga), for example, may be cultivated in an open pond environment for the production of microbial biomass for many different purposes, including energy, nutraceuticals and animal feed. The large-scale cultivation of organisms in open ponds, however, presents some formidable challenges including the harvesting of the biomass grown in the ponds. For photosynthetic micro-organisms, the ratio of biomass-to-liquid media produced may be very low, sometimes on a scale of only a few milligrams of biomass per liter. Accordingly, the costs associated with separating the biomass from the liquid media may be prohibitively expensive.

Exemplary embodiments of the present invention include novel cyanobacterial isolates found in the San Francisco Bay, that upon cessation of agitation, readily auto-flocculate and settle out of the growth media for inexpensive harvesting. The various embodiments as described herein present a biological platform for the production of renewable energy, plastic, chemicals and other materials.

Figure 1:
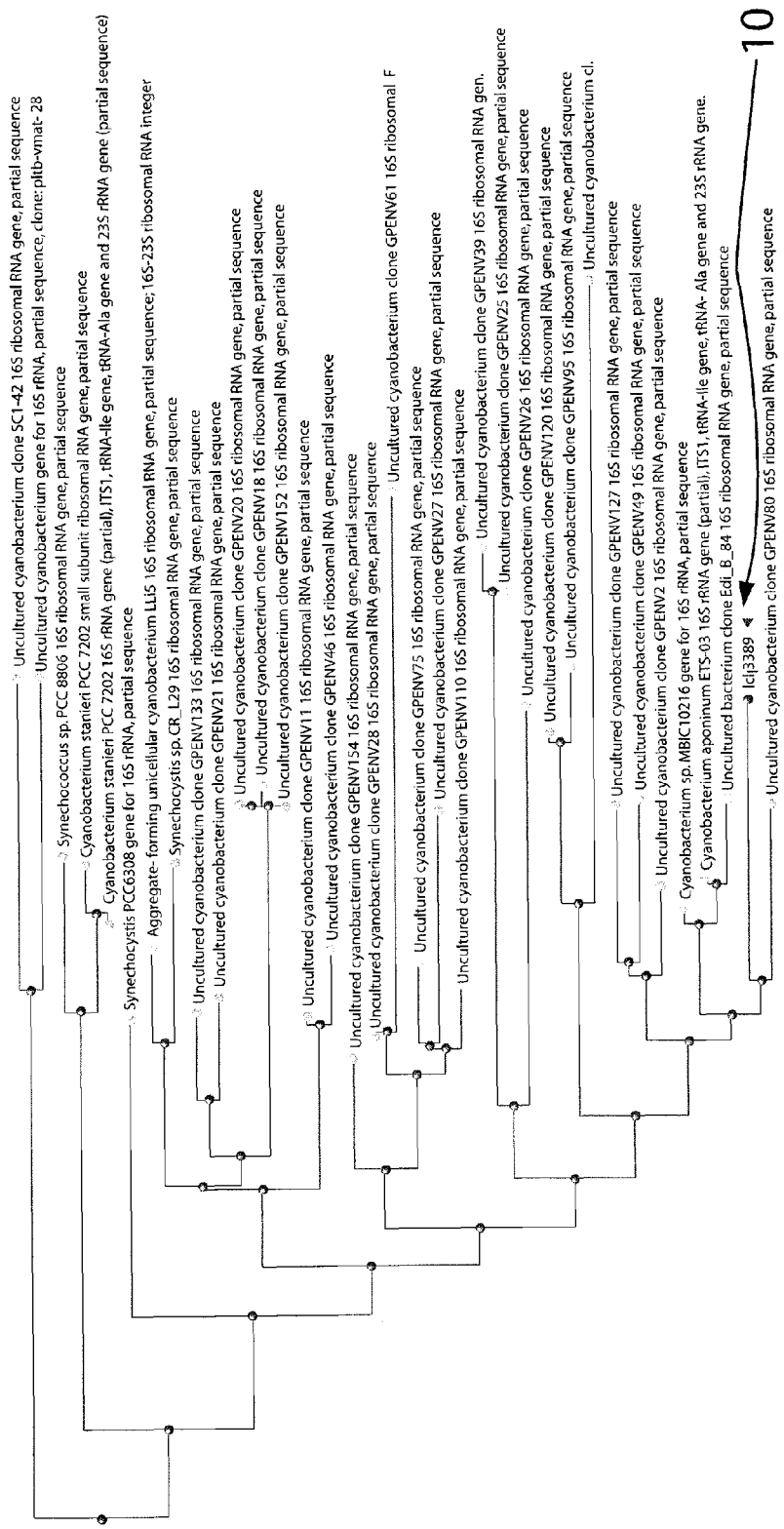
FIG. 1 shows a phylogenetic tree, which includes an exemplary cyanobacterial isolate.

FIG. 1 shows a phylogenetic tree, which includes an exemplary cyanobacterial isolate 10. FIG. 2 shows an exemplary 16S ribosomal RNA gene sequence (SEQ. ID. NO. 1) for an exemplary cyanobacterial isolate. Various exemplary cyanobacterial isolates as described herein may be found in the San Francisco Bay during the Summer Season. These exemplary cyanobacterial isolates grow as auto-flocculated clumps. When agitation of a cyanobacterial isolate culture ceases, cyanobacterial biomass settles out of the liquid media within minutes, without the application of a flocculant, a coagulant, a pH change and/or another physiological or biochemical machination. The settling properties of these exemplary cyanobacterial isolates make them an attractive platform for the production of biofuel feedstocks (lipids and starches), raw biomass, production of renewable plastic feedstocks such as polyhydroxybutyrates (PHB), polyhydroxyalkanoates (PHA) and polylactides (PLA) and/or other chemicals or materials. Additionally, these exemplary cyanobacterial isolates grow with a biomass productivity that matches or exceeds the productivity of algal strains that are currently used for industrial purposes. The inventors found some of the exemplary cyanobacterial isolates described herein had an average biomass productivity of ~900 mg/l/day, as estimated at ~400 µE/(m2*d) light irradiance in Roux bottles (e.g. Pyrex® Roux culture bottle 1000 ml) exposed with one side to the light source and filled with 800 ml algae culture and daily dilutions by 50%.

Figure 3:
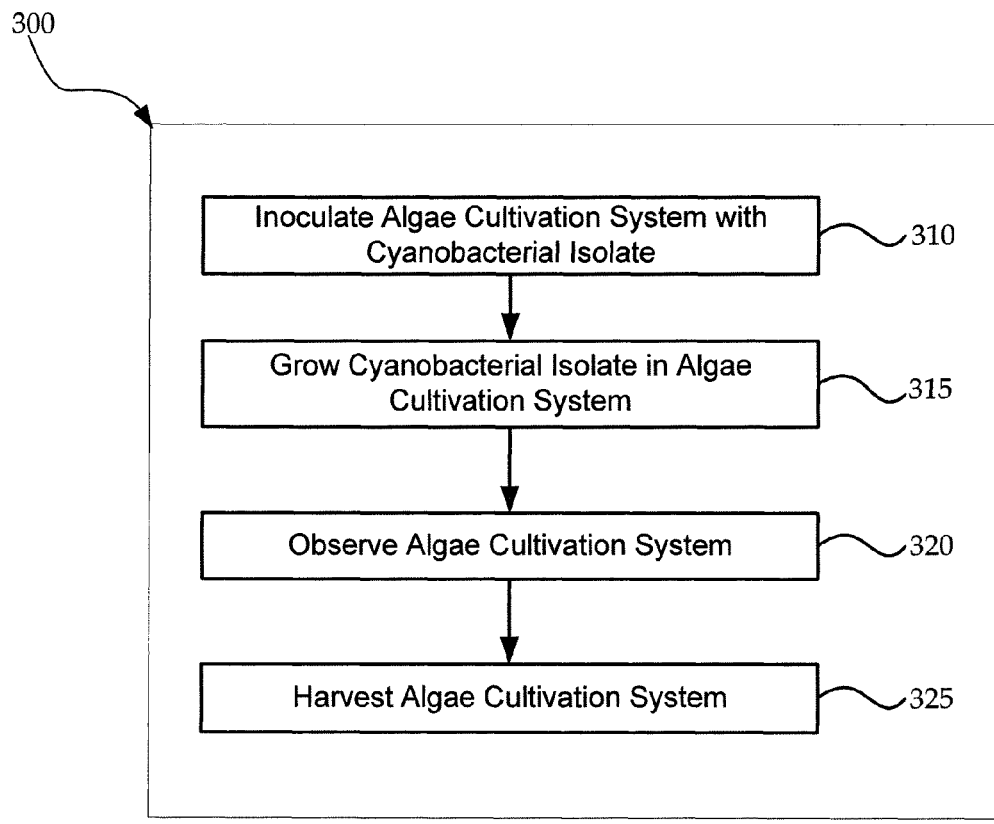
FIG. 3 shows a flow chart for an exemplary method of producing biomass with an exemplary cyanobacterial isolate in an algae cultivation system.

FIG. 3 shows a flow chart for an exemplary method 300 of producing biomass with an exemplary cyanobacterial isolate in an algae cultivation system.

At step 310, the algae cultivation system is inoculated with an exemplary cyanobacterial isolate (note: step 310 may be skipped if an exemplary cyanobacterial isolate is already present, e.g., an existing pond). According to one exemplary embodiment, the algae cultivation system is inoculated with the exemplary cyanobacterial isolate 10 having the phylogenetic tree shown in FIG. 1, and which includes the exemplary 16S ribosomal RNA gene sequence (SEQ. ID. NO. 1) shown in FIG. 2. The cyanobacterial isolate culture may be started with the addition of an initial, small amount of pure unialgal (virtually free from unwanted contaminant organisms) cyanobacterial isolate. Such an inoculum may be generated in a controlled environment, such as in a laboratory or in a closed system.

At step 315, the cyanobacterial isolate is grown in the algae cultivation system. According to various embodiments, the cyanobacterial isolate culture may require light (natural or artificially supplied) for growth, as well as nutrients. Other parameters such as pH should be within acceptable ranges. The basic elements typically required for cyanobacterial isolate growth may include carbon, oxygen, hydrogen, nitrogen, sulfur, phosphorous, potassium, magnesium, iron and traces of several other elements. Table 1 below shows an exemplary UFM media formulation for the growth of various exemplary cyanobacterial isolates.

TABLE 1

| Ingredient | Concentration (per liter basis) |
| --- | --- |
| $CO_2$ | 1% in air (bubbling to achieve pH of 7-8.5) |
| Seawater formulation (Instant Ocean) | 35 g |
| Urea | 720 mg |
| $K_2HPO_4$ | 168 mg |
| F/2 metals (PROLINE Solution A) | 1 ml |
| B12 | 1 mg |
| Biotin | 1 mg |
| Thiamine | 200 mg |

The required nutrients for cyanobacterial isolate growth may be contained in the water, supplied subsequently in dilution waters, or supplied independently of the dilution waters, in a concentration sufficient to allow the cyanobacterial isolate to grow and reach a desired final density. The amount of nutrients needed to yield a prescribed cyanobacterial isolate density may be determined by the cell quota for that nutrient. That is, by the percent of the algal dry mass that is comprised of the element contained in the nutrient. The inverse of the cell quota is called the algae growth potential for that nutrient or element. For instance, if the desired final density is 1 gram/liter and if the cyanobacterial isolate strain under consideration contains ten percent (10%) nitrogen in its biomass (i.e., a cell quota of 0.1), then the initial concentration of the atomic nitrogen in the culture should be at least 0.1 gram/liter. The same calculation may be performed for all nutrients to establish their initial concentration in the culture.

In various embodiments, the time-averaged light intensity to which a cyanobacterial isolate may be exposed may be adjusted by changes in the mixing intensity and/or in the optical depth of the pond. The optical depth in open ponds may be the depth of the pond. In open ponds, the temperature may be controlled by adjusting culture depth. After two to ten days, a cyanobacterial isolate may reach a productive operating density depending on light intensity, temperature, and the starting inoculum size.

Once the cyanobacterial isolate is grown to a desired density, according to some embodiments, it may either be removed (and a new culture may be started with a new inoculum), or it may be diluted according to a prescribed schedule or rate. In the first case, culturing may be performed in a batch mode and may require frequent re-inoculation. In the latter case, culturing may be performed in a continuous or a semi-continuous fashion, depending on the way the dilution is performed. For example, assuming that the desired dilution rate is fifty percent (50%) per day of the culture volume, culture dilution may take place in one or more of several techniques. Culture dilution may take place continuously over the day (or over part of the day) at a constant or at a variable rate. Culture dilution may alternatively take place semi-continuously once a day (i.e., fifty percent (50%) of the culture is removed and replaced with a new growth medium in a short period of time every day); semi-continuously twice a day (i.e., twenty-five percent (25%) of the culture is removed each time at two different times every day); or semi-continuously at any other desired frequency over the day. In some embodiments, culture dilution may comprise removing the cyanobacterial isolate culture medium from the growth system and replacing this portion with fresh medium, which may contain all of the nutrients in the quantity sufficient for the growth of the cyanobacterial isolate between two consecutive dilutions.

At step 320, after the algae cultivation system is inoculated with the cyanobacterial isolate and the cyanobacterial isolate is grown to a desired density (e.g., as described in connection with step 310 and step 315), the algae cultivation system may be observed (e.g., visually with a naked eye, microscopically, and/or analytically, including the taking and analysis of samples). Such observations or sampling may take place every minute, hourly, daily, every other day, three times a week, weekly, and/or on any other suitable basis. In connection with this process, one or more determinations may be made as to a relative level or amount of predators and/or invaders in comparison to an actual and/or desired density or dominance of the cyanobacterial isolate.

At step 325, the algae cultivation system is harvested. According to one exemplary embodiment, the cyanobacterial isolates grow as free cells auto-flocculating to clumps. When agitation of the cyanobacterial culture ceases, cyanobacterial biomass flocculates and settles out of the liquid media within minutes, even without the application of a flocculant, a coagulant, a pH change and/or another physiological or biochemical machination.

While various embodiments have been described herein, it should be understood that they have been presented by way of example only, and not limitation. Thus, the breadth and scope of a preferred embodiment should not be limited by any of the above-described exemplary embodiments.

What is claimed is:

1. A method for production of biomass with a cyanobacterial isolate having auto-flocculation properties, the method comprising:

isolating a cyanobacterial strain having a 16S ribosomal RNA sequence corresponding to SEQ. ID. NO. 1;

inoculating an algae cultivation system with the cyanobacterial strain having the 16S ribosomal RNA sequence corresponding to SEQ. ID. NO. 1;

growing the cyanobacterial strain having the 16S ribosomal RNA sequence corresponding to SEQ. ID. NO. 1 in the algae cultivation system; and harvesting the biomass produced by the cyanobacterial strain.

2. The method of claim 1, wherein the harvesting of the biomass comprises:

ceasing agitation of the algae cultivation system; and pooling a slurry of the biomass produced by the cyanobacterial strain having the 16S ribosomal RNA sequence corresponding to SEQ. ID. NO. 1.

3. The method of claim 1, wherein the harvesting of the biomass comprises:

ceasing agitation within the algae cultivation system.

4. The method of claim 3, wherein the harvesting of the biomass comprises:

allowing the biomass produced by the cyanobacterial strain having the 16S ribosomal RNA sequence corresponding to SEQ. ID. NO. 1 to settle to near or at a bottom of the algae cultivation system.

* * * * *